(12) United States Patent
Nalesso et al.

(10) Patent No.: US 8,771,234 B2
(45) Date of Patent: Jul. 8, 2014

(54) SYRINGE FOR SEQUENTIAL EXPRESSION OF DIFFERENT LIQUIDS

(75) Inventors: Federico Nalesso, Padua (IT); Mark S. Fisher, Sellersville, PA (US); William Shaun Wall, North Wales, PA (US)

(73) Assignee: Medical Components, Inc., Harleysville, PA (US)

( * ) Notice: Subject to any disclaimer, the term of this patent is extended or adjusted under 35 U.S.C. 154(b) by 0 days.

(21) Appl. No.: 13/177,169

(22) Filed: Jul. 6, 2011

(65) Prior Publication Data

US 2012/0016313 A1    Jan. 19, 2012

Related U.S. Application Data

(63) Continuation of application No. 11/983,531, filed on Nov. 9, 2007, now Pat. No. 8,021,343.

(30) Foreign Application Priority Data

Nov. 13, 2006   (IT) .............................. PD2006A0419

(51) Int. Cl.
*A61M 5/00* (2006.01)
*A61M 5/178* (2006.01)

(52) U.S. Cl.
USPC ....................................... 604/191; 604/167.03

(58) Field of Classification Search
USPC ............... 604/82, 86–89, 187, 191, 201, 203, 604/205, 241, 244, 416, 167.03
See application file for complete search history.

(56) References Cited

U.S. PATENT DOCUMENTS

| | | | |
|---|---|---|---|
| 3,563,240 A | | 2/1971 | Silver |
| 3,826,260 A | * | 7/1974 | Killinger ........................ 604/413 |
| 3,911,916 A | | 10/1975 | Stevens |
| 4,178,928 A | | 12/1979 | Tischlinger |
| 4,232,669 A | * | 11/1980 | Nitshke ......................... 604/192 |

(Continued)

FOREIGN PATENT DOCUMENTS

FR   2612782 A1   9/1988
WO  2006/099441 A2   9/2006

OTHER PUBLICATIONS

International Preliminary Report on Patentability dated Aug. 3, 2011; PCT Application No. PCT/US2007/023654 (15 pages).

(Continued)

*Primary Examiner* — Kevin C Sirmons
*Assistant Examiner* — William Carpenter
(74) *Attorney, Agent, or Firm* — Glenn M. Massina, Esq.; Fox Rothschild LLP

(57) ABSTRACT

A device (10,110,210) for the expression of liquids, such as for the maintenance treatment of vascular catheters. A syringe (16;116a,116b;216) has a support structure (15,215) and includes at least two separate compartments (11,12;111,112; 211,212) in which liquids for treating the lumen (L,283) of a catheter (C,280) with which the device is associated. The syringe further includes a closure plug (13,213) to be associated with the lumen being treated, which is coupled, by virtue of a releasable securement arrangement, to support structure (15,215). At least one plunger (16;116a,116b;216) is also included for infusing, in preset order, the different treatment liquids into the lumen to be treated, and the syringe further includes a duct (17,217) which is in fluid communication with the two compartments and is arranged through a through hole through the closure plug (13,213) in order to allow access of the treatment liquid to the interior of the lumen (L,283) upon activation of the plunger.

6 Claims, 10 Drawing Sheets

(56) References Cited

U.S. PATENT DOCUMENTS

| | | | |
|---|---|---|---|
| 4,367,739 A | 1/1983 | LeVeen et al. | |
| 4,710,179 A | 12/1987 | Haber et al. | |
| 4,887,998 A | 12/1989 | Martin et al. | |
| 4,915,697 A | 4/1990 | DuPont | |
| 4,917,672 A | 4/1990 | Terndrup et al. | |
| 4,917,679 A | 4/1990 | Kronner | |
| 4,932,944 A * | 6/1990 | Jagger et al. | 604/191 |
| 4,998,925 A * | 3/1991 | Al-Sioufi et al. | 604/533 |
| 4,998,927 A * | 3/1991 | Vaillancourt | 604/537 |
| 5,102,388 A | 4/1992 | Richmond | |
| 5,120,324 A * | 6/1992 | Sancoff | 604/533 |
| 5,139,483 A * | 8/1992 | Ryan | 604/86 |
| 5,273,540 A | 12/1993 | Luther et al. | |
| 5,279,581 A | 1/1994 | Firth et al. | |
| 5,298,024 A | 3/1994 | Richmond | |
| 5,344,407 A | 9/1994 | Ryan | |
| 5,344,409 A | 9/1994 | Ennis, III et al. | |
| 5,376,073 A * | 12/1994 | Graves et al. | 604/86 |
| 5,437,650 A * | 8/1995 | Larkin et al. | 604/536 |
| 5,476,449 A | 12/1995 | Richmond | |
| 5,514,117 A * | 5/1996 | Lynn | 604/536 |
| 5,540,667 A | 7/1996 | Tanner, II | |
| 5,607,392 A * | 3/1997 | Kanner | 604/86 |
| 5,658,260 A * | 8/1997 | Desecki et al. | 604/239 |
| 5,827,262 A * | 10/1998 | Neftel et al. | 604/414 |
| 6,022,339 A * | 2/2000 | Fowles et al. | 604/411 |
| RE36,885 E | 9/2000 | Blecher et al. | |
| 6,159,184 A | 12/2000 | Perez et al. | |
| 6,217,568 B1 * | 4/2001 | Jepson et al. | 604/533 |
| 6,423,050 B1 | 7/2002 | Twardowski | |
| 6,524,278 B1 * | 2/2003 | Campbell et al. | 604/192 |
| 6,562,007 B1 | 5/2003 | Falsey | |
| 6,719,719 B2 | 4/2004 | Carmel et al. | |
| 6,730,062 B2 | 5/2004 | Hoffman et al. | |
| 6,824,529 B2 | 11/2004 | Gross et al. | |
| 6,830,560 B1 | 12/2004 | Gross et al. | |
| 6,843,782 B2 | 1/2005 | Gross et al. | |
| 6,966,898 B1 | 11/2005 | Pouget et al. | |
| 6,966,899 B2 | 11/2005 | Hochman et al. | |
| 7,195,623 B2 * | 3/2007 | Burroughs et al. | 604/411 |
| 7,351,224 B1 | 4/2008 | Shaw | |
| 8,152,778 B2 | 4/2012 | Chebator | |
| 2001/0051793 A1 * | 12/2001 | Weston | 604/232 |
| 2002/0062107 A1 | 5/2002 | Parmigiani et al. | |
| 2002/0092524 A1 | 7/2002 | Lockhart et al. | |
| 2002/0189705 A1 * | 12/2002 | Reihl et al. | 141/27 |
| 2003/0023203 A1 | 1/2003 | Lavi et al. | |
| 2003/0060781 A1 | 3/2003 | Mogensen et al. | |
| 2003/0105430 A1 | 6/2003 | Lavi et al. | |
| 2003/0236503 A1 | 12/2003 | Koenig et al. | |
| 2004/0138612 A1 | 7/2004 | Shermer et al. | |
| 2004/0186547 A1 | 9/2004 | Dorn et al. | |
| 2004/0260266 A1 * | 12/2004 | Cuschieri et al. | 604/411 |
| 2005/0192545 A1 | 9/2005 | Voorhees et al. | |
| 2007/0073267 A1 | 3/2007 | Muller | |

OTHER PUBLICATIONS

International Search Report, PCT/US2007/023654, dated Jul. 7, 2008 (6 pages).

Written Opinion, PCT/US2007/023654, dated Jul. 7, 2008 (8 pages).

* cited by examiner

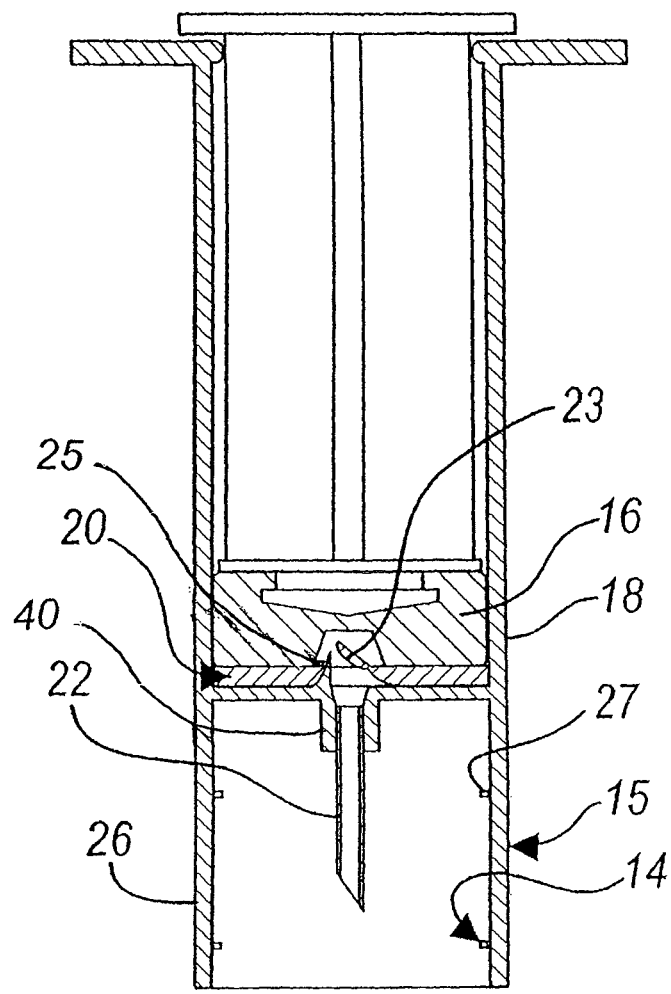
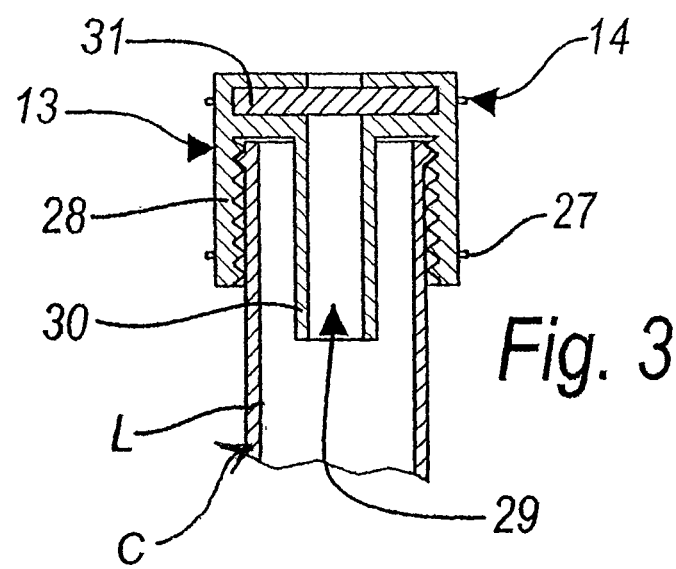
Fig. 3

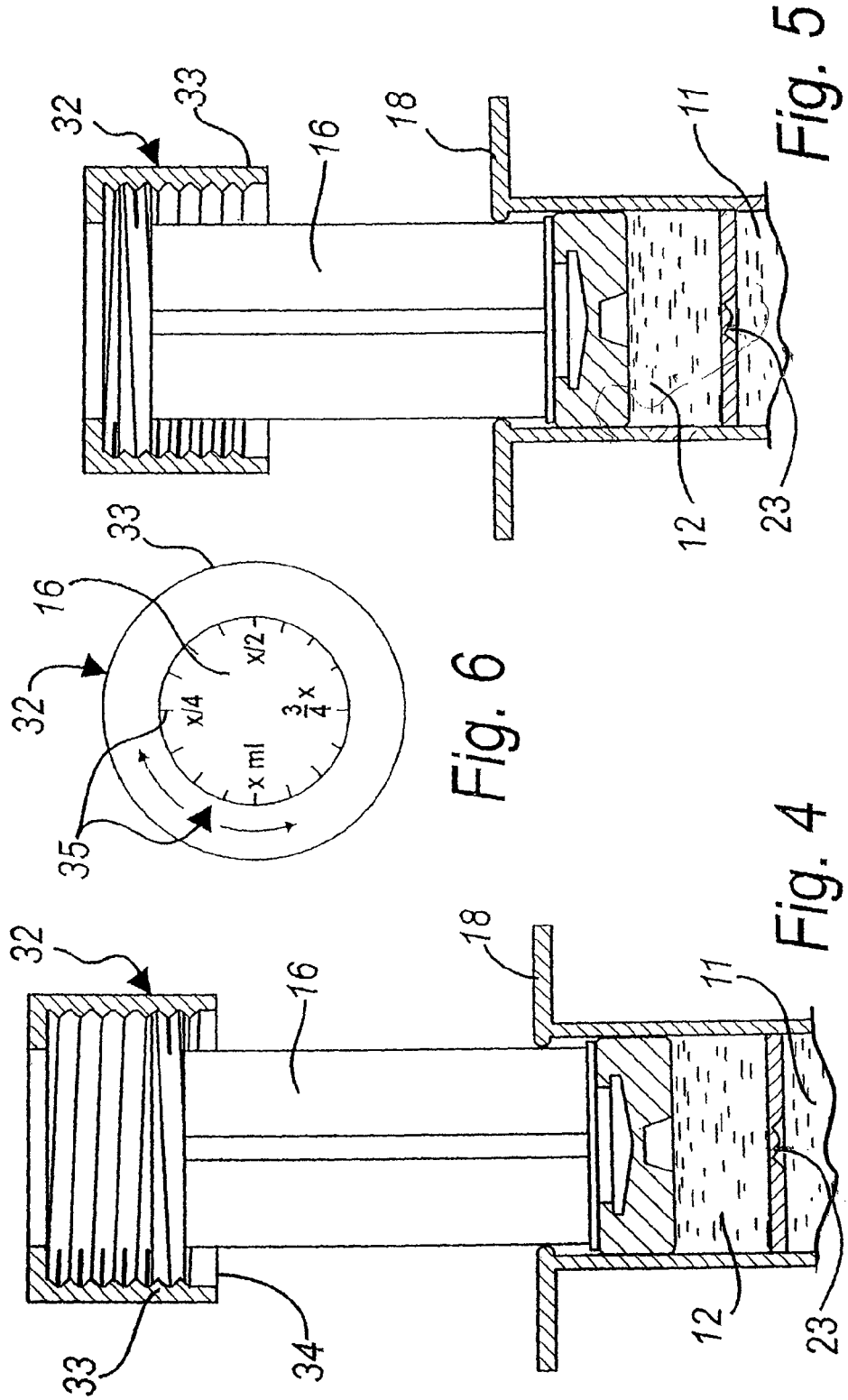

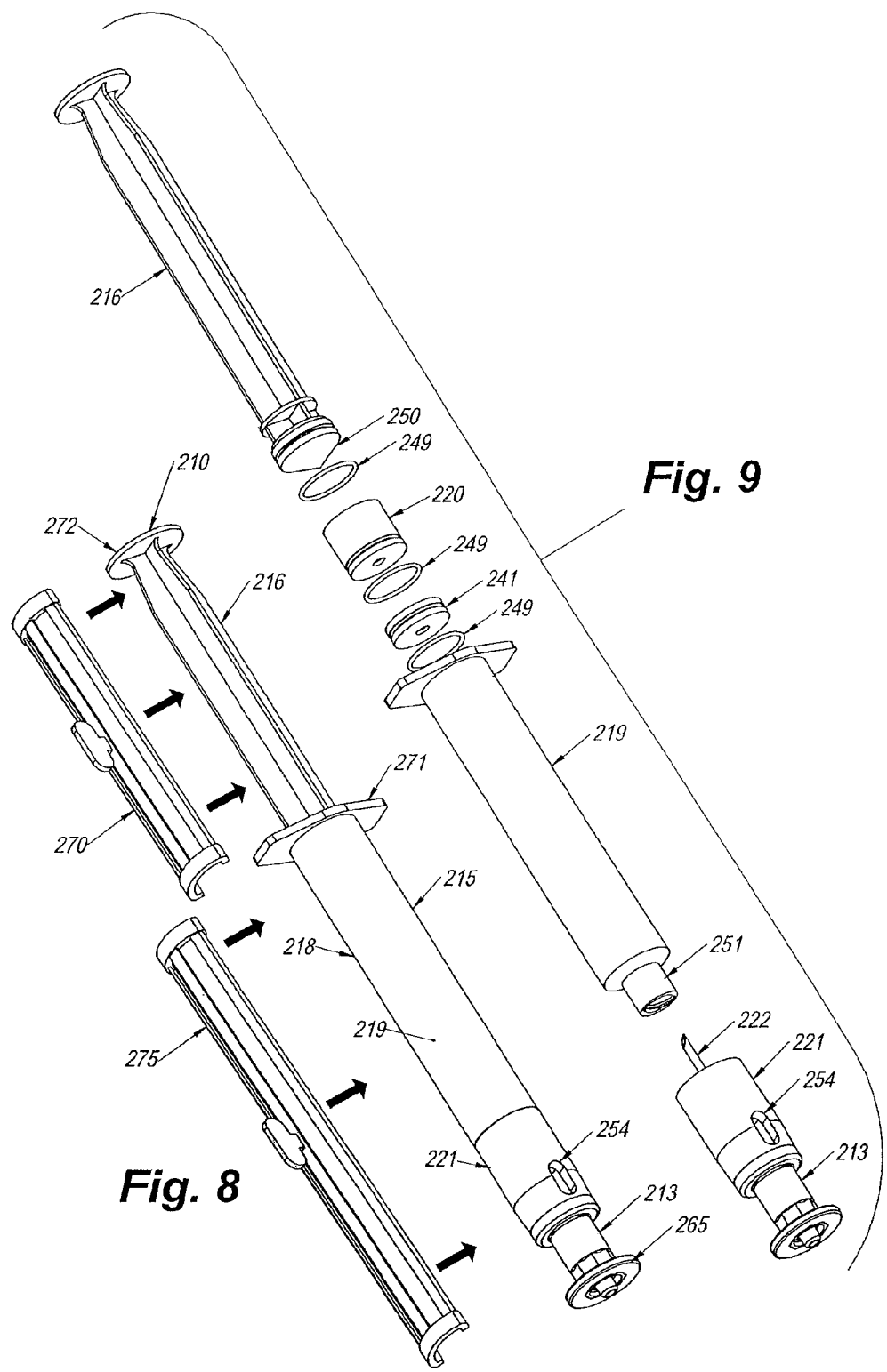

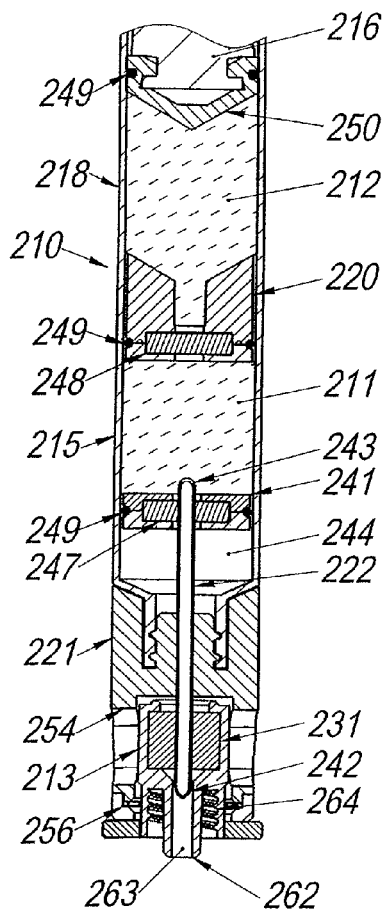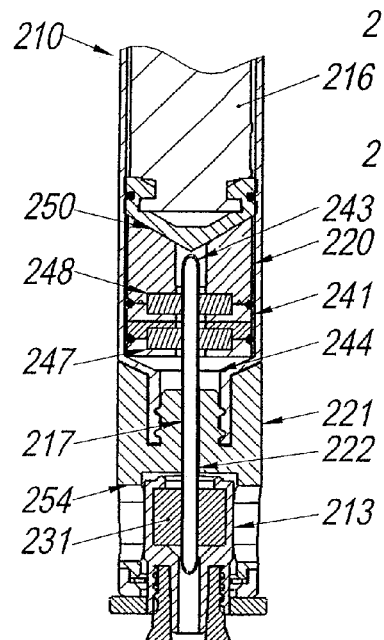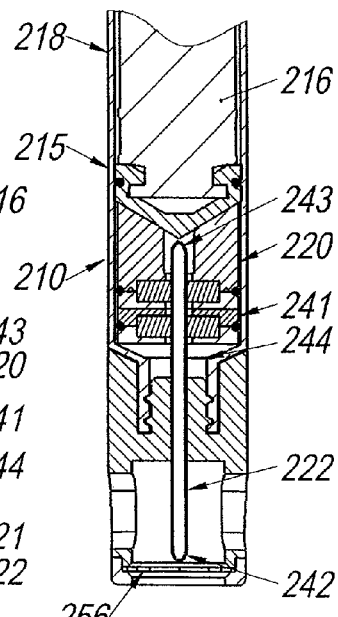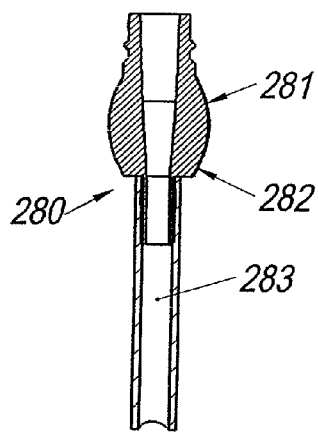
FIG. 18
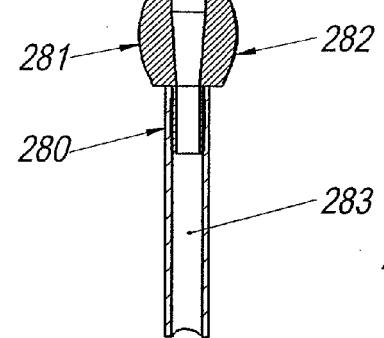
FIG. 19
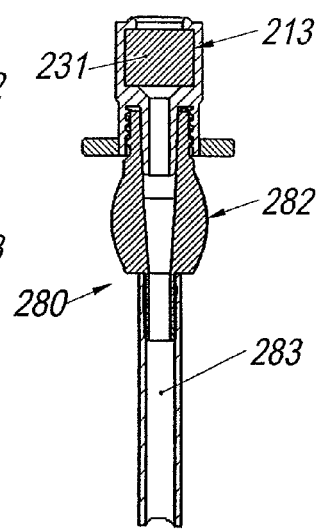
FIG. 20

SYRINGE FOR SEQUENTIAL EXPRESSION OF DIFFERENT LIQUIDS

CROSS-REFERENCE TO RELATED APPLICATIONS

This application is a Continuation application of U.S. Ser. No. 11/983,531 filed Nov. 9, 2007 which in turn claims priority from Italian patent application No. PD2006A000419 filed Nov. 13, 2006.

FIELD OF THE INVENTION

This relates to the field of medical devices, and more particularly to syringes.

BACKGROUND OF THE INVENTION

As is known, vascular catheters, including central venous catheters, or CVCs, are medical devices for the infusion of pharmacological substances and fluids into a vessel of a patient, for example, the inner jugular, the subclavian, and the femoral vein, and for performing extracorporeal blood circulation during hemodialysis or other procedures which require extracorporeal blood circulation. Such vascular catheters can include, depending upon the operating requirements, one or more lumens; single-lumen, dual-lumen and triple-lumen catheters are generally used.

The classical application of dual-lumen or triple-lumen catheters relates to extracorporeal circulation for performing chronic extracorporeal hemodialysis, such as for patients which chronic kidney failure, and for performing continuous renal replacement therapy, or CRRT, in critically ill patients in intensive care units. Single-lumen catheters are used to infuse drugs and liquids, to draw blood samples and to monitor pressures in certain vascular regions.

Catheters can be of two main types: temporary and permanent. Temporary catheters are those which are placed for limited periods of time in patients who have acute requirements, whereas permanent catheters are placed to ensure chronic therapies and can have a working life of over three years. Since permanent catheters must ensure higher safety due to their permanent nature, they are provided with a subcutaneous portion between the entrance into the vein and the exit from the skin, so as to minimize the possible infections to which the patient is exposed. Any manipulation of any kind of central venous catheter, if not performed in fully aseptic conditions, can expose the patient to even fatal infection, since the CVC is placed in a central vein. Maintenance of the catheters after each use in a medical procedure is therefore particularly important in order to avoid infections and dysfunctions thereof.

In addition to the problem of infection, catheters, by being in contact with blood, are in fact exposed to coagulation of the blood at the location of the openings of the lumens. Coagulation in the catheter lumen therefore causes malfunction thereof or even complete blockage of the catheter, with the consequent need to replace it in order to continue the medical therapies in progress. Currently, the lumen or lumens of the catheter, after each use, are washed by infusing thereinto physiological solution and are then medicated by infusing thereinto an anticoagulant in order to avoid coagulation therewithin, which anticoagulant expresses the physiological solution from the catheter lumens into the vasculature. The anticoagulant is subsequently evacuated by vacuum from the catheter's proximal end when next the catheter is to be used for hemodialysis. Since the anticoagulant must remain in place and must not enter the blood circulation of the patient, in order to avoid anticoagulation within the vasculature of the patient, the volume of anticoagulant applied to each catheter lumen used must match exactly the volume of the lumen used in the procedure.

Currently, health workers who close a catheter are required to perform the following procedures for each lumen of the catheter: open a sterile syringe; open the vial of physiological solution; aspirate the physiological solution into the syringe; disconnect the device connected to the lumen of the catheter, such as an infusion syringe or tubing for dialysis or for extracorporeal circulation in other medical contexts; connect the syringe; infuse the physiological solution to perform washing; disconnect the syringe; open another sterile syringe, open the vial of anticoagulant solution; aspirate the anticoagulant solution into the syringe, paying particular attention to the aspirated volume; connect the syringe to the catheter lumen; infuse the anticoagulant in the exact filling volume of the lumen; disconnect the syringe; and apply the closure plug to the catheter lumen.

As is evident from this sequence of operations, the maintenance procedure of a catheter is time-consuming and laborious. In view of the laboriousness, the risk of procedural errors on the part of an operator is obviously high. Typical errors can be, for example, the use of incorrect products in solution, the infusion of incorrect quantities, errors in connecting parts of the catheter, and so forth. In addition to the possibility of errors, which can lead to the need to remove the catheter or, in the worst case, to actions which damage the health of the patient, the time-related aspects of the operations that must be performed also have to be considered. The maintenance time of a catheter is in fact not negligible, and if it is necessary to perform this operation frequently, as in the case of a large number of patients, the total time is important and must be assessed in terms of management expense of the hospital ward.

The aim of the present invention is to solve the problems linked to the maintenance of vascular catheters as described above. It is desired to reduce the number of operations linked to the maintenance of vascular catheters. It is also desired to reduce maintenance time with respect to maintenance of vascular catheters.

It is also desired to provide a device for catheter maintenance that is easy to use, that is safe for the practitioner and reliable in operation, and that is flexible in its use.

It is also desired to provide such a device that enables avoidance of infection risk and of anticoagulation phenomena in the patient.

BRIEF SUMMARY OF THE INVENTION

Briefly, one key aspect of the present invention is a device that achieves the aforesaid desires and objectives, particularly for catheter maintenance. The device comprises a syringe having a support structure, two (or more) separate compartments in which respective liquids for lumen treatment are contained, a duct proximate the distal end which is in fluid communication with the compartments and extends through the syringe's distal end wall, and at least one plunger at the proximal end for infusing, according to a preset order, the different treatment liquids into the lumen by applying pressure to the liquid when the plunger is activated by the practitioner. The inventive syringe also enables sequential expression of different liquids into other medical devices.

In one embodiment, there are two compartments arranged in series within the chamber of the syringe's support structure, along with a single plunger. A movable partition separates the compartments; a distal wall provides an outer end to the first compartment, while the plunger provides the outer end of the second compartment. Activation of the plunger applies pressure to the liquid in the second, or proximal, of the two compartments which relays pressure to the movable partition which in turn pressurizes the liquid in the first or distal of the compartments to express liquid from the first compartment firstly; when the movable partition approaches the distal wall, a piercing lance of the distal wall pierces a pierceable portion of the movable partition to create an exit for liquid in the second compartment which then can access the duct and be expressed from the syringe into the lumen of the catheter.

In another embodiment, there are two compartments that are arranged in parallel, each with an associated plunger. A common access permits liquid from either compartment to be expressed through the duct at the distal end of the syringe.

Preferably, the syringe further includes a closure plug affixed to the support structure of the syringe at its distal end. The closure plug includes a through hole for fluid passage therethrough from the duct to the catheter lumen. The closure plug is adapted to be mechanically connected to a catheter proximal end in a manner such that the through hole establishes fluid communication with the catheter lumen. Preferably, the closure plug includes a penetrable sealing membrane traversing the through hole for sealing except when liquid is being expressed from the syringe into the catheter lumen. A needle affixed to the distal chamber wall penetrates this membrane when desired. Preferably, the closure plug is removably secured to the support structure in a plug-containing cavity by easily detachable connections or releasable securements such as frangible tabs, so that upon completion of the maintenance treatment of the catheter, the syringe may be removed from the catheter while the closure plug detaches from the syringe and remains on the catheter proximal end to close off the lumen.

In another embodiment, the syringe assembly is provided with compartments in series and an elongated needle with sharp tips at its proximal and distal ends, and within the syringe each compartment is provided with a movable partition as its distal wall containing a membrane that is pierceable by the needle's proximal tip to access the compartment for expression of liquid therefrom. A distal section is assembled to the distal end of the syringe assembly with a needle extending therethrough such that the needle's distal tip penetrates a plug member contained within a closure cap when the closure cap is inserted into a plug-receiving chamber of the distal section, for establishing fluid communication to express the liquids from the syringe upon activation of the plunger. The needle's proximal tip penetrates, in sequence, pierceable membranes of the two movable partitions to enable expression of liquid from the respective compartments upon activation of the plunger by the practitioner or medical technician.

The present invention is also of an arrangement for expression of liquid providing a support structure containing liquid and having a closure plug-receiving cavity and a closure plug receivable thereinto, where a medical device is securable to the closure plug for expression of liquid into the medical device, and where the closure plug is removable from the cavity for disconnection of the support structure from the medical device by the closure plug remaining secured to the medical device. The support structure is manually holdable and includes a manually operable plunger, and the closure plug is adapted to be securable to the support structure by a practitioner.

The present invention also comprises a method comprising the steps of:

providing a device having:
  a support structure having at least two separate compartments for containing respective liquids;
  a distal wall traversing the support structure proximate a distal end thereof;
  a duct extending through the distal wall enabling liquid to exit the at least two compartments; and
  at least one plunger movably affixed to the support structure proximate the proximal end thereof for infusing liquids from the device through the duct upon activation of the at least one plunger,
  the support structure, the at least two compartments and the at least one plunger being adapted to infuse the respective liquids sequentially in a preselected order into the catheter lumen;
providing a catheter having a lumen open at a proximal end of the catheter;
connecting the catheter proximal end to the distal end of the device such that the duct is in fluid communication with the lumen;
activating the at least one plunger to express a first liquid from a first compartment, through the duct and into the lumen;
activating one of said at least one plunger or another plunger associated with the second compartment, to express a second liquid from a second compartment through the duct and into the lumen; and
removing the device from the catheter proximal end.

The method may also preferably include providing such a device that further includes a closure plug removably attachable to the support structure at a distal end thereof, the closure plug being adapted to be connected to the catheter proximal end, so that the step of removing the device from the catheter proximal end comprises detaching the closure plug from the support structure while the closure plug remains connected to the catheter proximal end.

Additional characteristics and advantages of the device of the present invention will become evident hereinbelow. Furthermore, such a device as the present invention can also be used for other purposes where sequential expression of different liquids is desired from the same syringe, including expression of liquid into a medical device, thus not being limited to maintenance treatment of catheters.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 3 is a longitudinal sectional view of the device of FIG. 1 after infusion has been completed;

FIG. 4 is a view of a portion of the device of FIGS. 1 to 3 with a metering section for adjusting the amount of liquid to be infused in a first setting, applied thereto;

FIG. 5 is a view of a the device portion of FIG. 4 illustrating the metering section in a second setting, related to a smaller amount of liquid to be infused;

FIG. 6 is a the device portion of FIGS. 4 and 5 taken at right angles thereto, of the metering section;

FIG. 8 is an isometric cross-sectional view of a third embodiment of syringe of the present invention that includes an elongate needle, two movable partitions each with a pierceable membrane that is pierceable by the needle, a plunger, and a distal section secured to the distal end of the syringe assembly;

FIG. 9 is an exploded isometric view of the syringe assembly of FIG. 8;

FIGS. 18 to 20 are cross-sectional views of the distal end of the syringe assembly of FIGS. 8 to 17 showing, respectively, the distal section and the closure plug with the closure plug seated within the distal section with catheter proximal end positioned to be connected to the syringe assembly, the catheter proximal end connected, and the catheter proximal end with closure plug attached thereto after being disconnected from the syringe assembly at the completion of an infusion procedure.

DETAILED DESCRIPTION OF THE INVENTION

Figure 1:
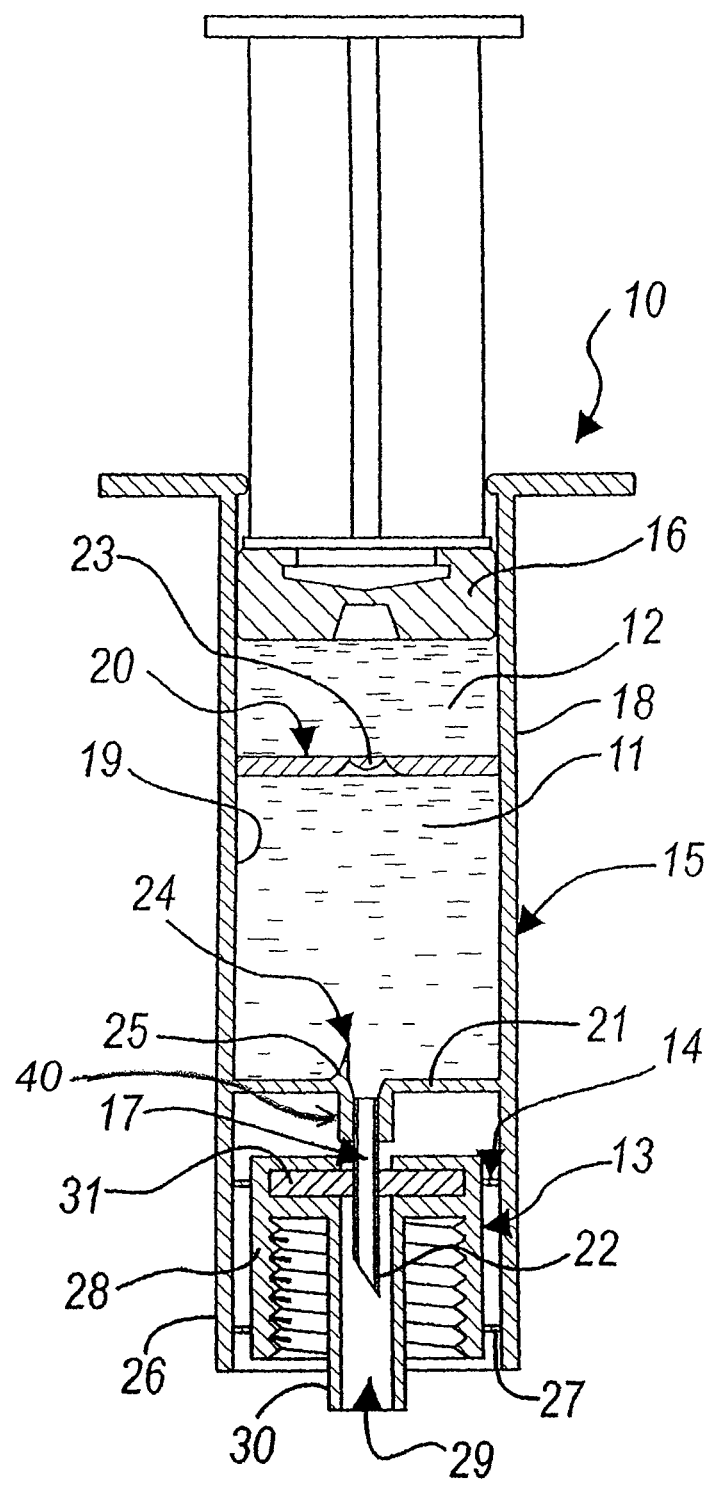
FIG. 1 is a longitudinal sectional view of a device according to the present invention.

In the drawings, like numerals indicate like elements throughout. Certain terminology is used herein for convenience only and is not to be taken as a limitation on the present invention. The terms "distal" and "proximal" refer, respectively, to directions closer to and away from the insertion tip of a catheter in an implantable catheter assembly. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Figure 2:
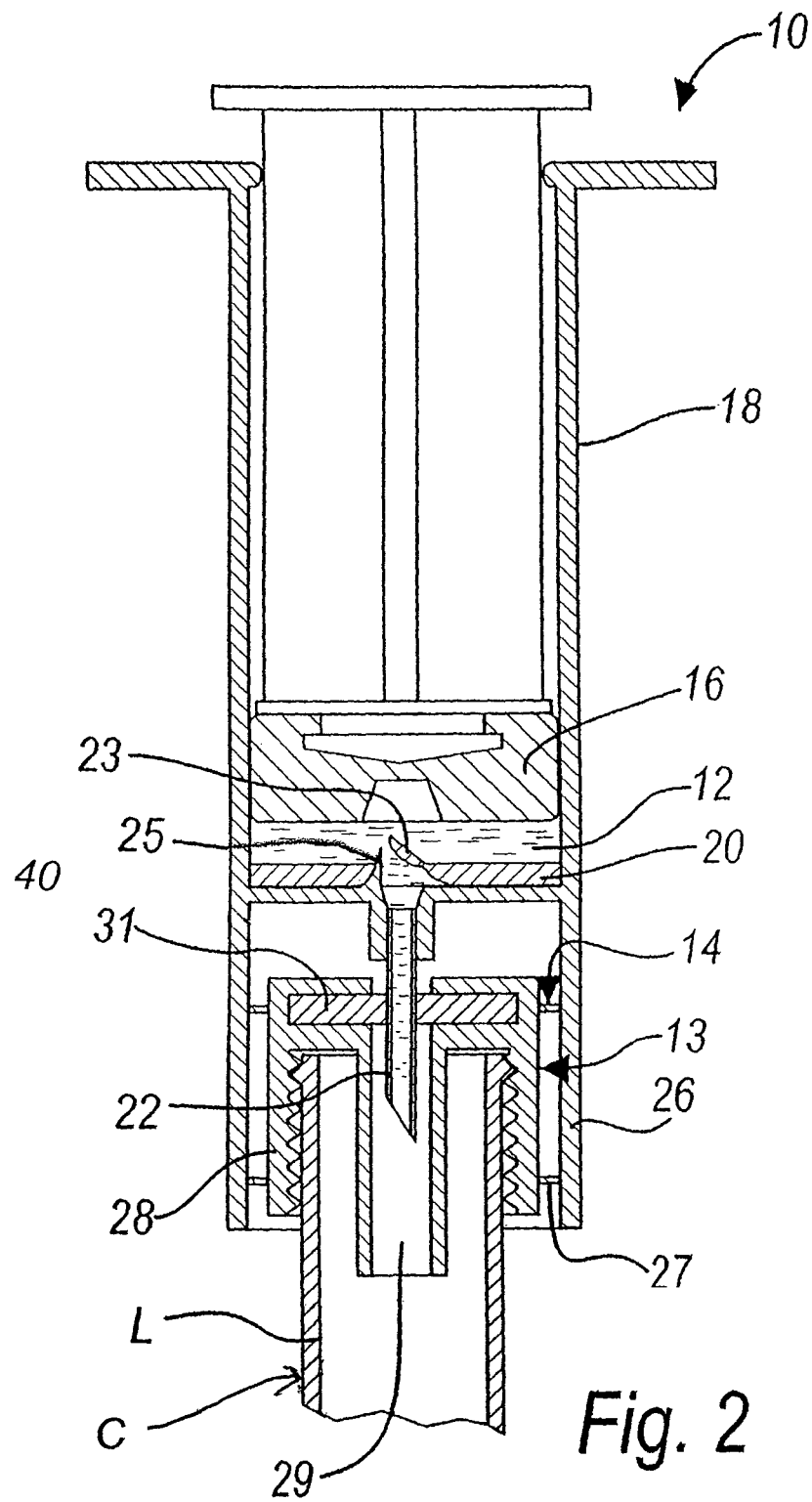
FIG. 2 is a longitudinal sectional view of the device of FIG. 1, shown during the final step of infusing the maintenance treatment liquids into a lumen of a catheter with which it is used.

With respect to FIGS. 1 to 3, a first embodiment of device 10 is shown, having a support structure 15 such as a syringe 18 having a cylindrical chamber 19, with a first compartment 11 and a second compartment 12. A physiological solution is present in the first compartment 11, and an anticoagulant liquid is present in the second compartment 12. Device 10 also preferably includes a closure plug 13 to be associated with the lumen L of a catheter C (see FIGS. 2 and 3) being treated, whose proximal end is coupled to support structure 15 by virtue of a releasable securement arrangement 14.

The device 10 further includes a plunger 16 and a duct 17. A duct 17 is in fluid communication with the first compartment 11, and ultimately to the second compartment 12, and extends through the closure plug 13; the duct preferably includes therethrough a preferably non-coring needle 22 that is rigidly coupled to and extends through the bottom wall 21 of chamber 19 of syringe 18, needle 22 being stabilized by and within axially extending flange 40 projecting distally (i.e., toward the catheter lumen L) from bottom or distal chamber wall 21. Activation of the plunger 16 will infuse liquid from the syringe into the interior of the lumen L of the catheter at the proximal end thereof, firstly the physiological liquid and subsequently the anticoagulant liquid, in preset order, thus treating the catheter lumen. One example of a physiological liquid is saline; one example of an anticoagulant is heparin.

First and second compartments 11, 12 are separated from each other by a partition 20 that is movable within cylindrical chamber 19. First compartment 11 is defined between the bottom chamber wall 21 and the movable partition 20, while second compartment 12 is defined between movable partition 20 and plunger 16. Movable partition 20 includes a pierceable portion 23, which once pierced allows the liquid present in the second compartment 12 to flow out through duct 17 and needle 22 and into the lumen as activation of the plunger is continued. Piercing is accomplished such as by piercing lance 24 defined by a pointed portion 25 protruding proximally from the bottom chamber wall 21, toward movable partition 20. Such piercing occurs when movable partition 20, pushed by plunger 16, is translated toward bottom chamber wall 21 and pierceable portion 23 is pressed against pointed portion 25 and is pierced thereby. Piercing allows the passage of the anticoagulant liquid to and through the duct 17 and ultimately to the lumen L, as is clear from FIG. 2.

In this embodiment, support structure 15 also comprises a plug-containing cavity 26 inside of which the closure plug 13 is initially secured by a releasable securement arrangement 14. The releasable securement arrangement may for example be frangible tabs 27 made of plastic material, and which lie between the internal wall of the plug-containing cavity 26 and the outside of plug 13. Tabs 27 are adapted to be broken with a rotary motion of the support structure 15 with respect to closure plug 13 when the plug is fixed to the proximal end of the catheter at lumen L. Simply put, the closure plug transfers from the syringe to the catheter proximal end during disconnection of the syringe from the catheter to continue sealing the catheter lumen thereafter until being later removed.

Needle 22 lies within plug-containing cavity 26 and is sufficiently short for its sharp distal end to be recessed entirely within cavity 26; as a result, the needle does not protrude from the syringe once the closure plug 13 is removed, for the safety to the operator. The closure plug 13, in this embodiment, may be a bushing 28 that is internally threaded for coupling to the complementarily threaded end portion of lumen L, such as would be provided by a conventional luer connector (not shown) affixed to the catheter proximal end.

Bushing 28 includes a centrally disposed tubular portion 30 through which is defined a passage or through hole 29; through hole 29 is aligned with lumen L when tubular portion 30 is received into the proximal end of lumen L after the device 10 is affixed to the proximal end of catheter C as seen in FIG. 1. Bushing 28 further includes a transverse sealing membrane 31 of self-sealing material which is conventionally known, such as of silicone material. Membrane 31 can be pierced by needle 22 passing therethrough during activation of the device (FIG. 2), and seals itself after needle 22 is withdrawn, as seen in FIG. 3, recovering the continuity interrupted by the needle, thus ensuring a barrier to the entrance of pathogenic agents into the lumen. Subsequently, it is possible to again pierce the membrane with the needle of the infusion syringe, when it is necessary to infuse drugs into the catheter, and as before the membrane reseals itself once the needle is extracted upon removal of the syringe from the catheter.

Advantageously, the device 10 also comprises a metering section 32 for adjusting the amount of treatment liquid that is present in at least one of the compartments 11 and 12, as is depicted in FIGS. 4 to 6. In particular, metering section 32 is constituted by an internally threaded ring 33, which is screwed onto the proximal end portion of plunger 16 accessible to the practitioner. Ring 33 forms an adjustable stroke limit 34 for the plunger, which is suitable to abut against the proximal end of the syringe body 18.

Graphic references or indicia 35 are provided on ring 33 and plunger 16 that cooperate with each other to indicate the amount of liquid that is desired to be infused into the lumen. As clearly shown in FIGS. 4 to 6, a rotation of ring 33 raises or lowers the stroke limit 34 of plunger 16, thus limiting its stroke by an amount which is indicated by the indicia provided between the ring and the plunger.

Figure 7:
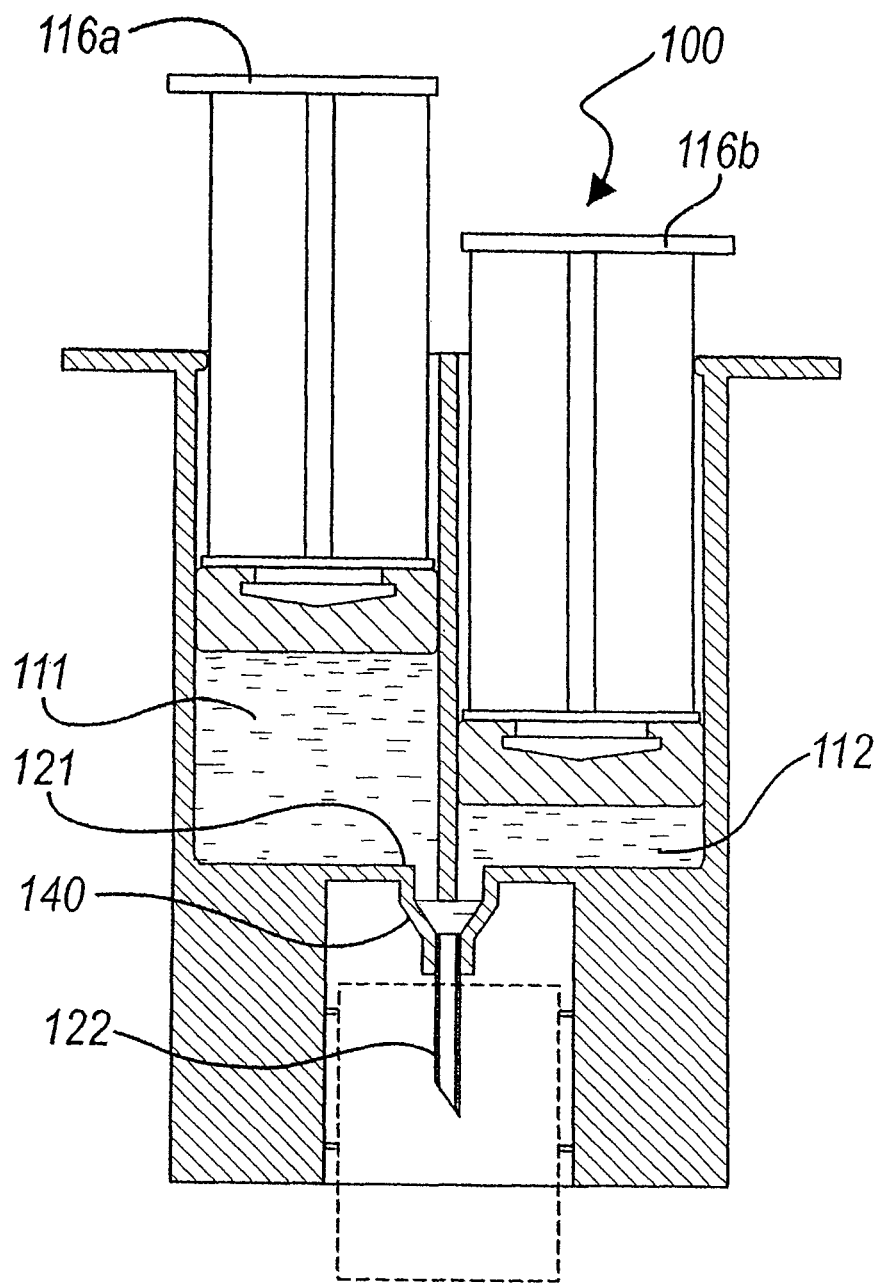
FIG. 7 is a view of another embodiment of the inventive device having dual plungers and compartments in parallel and having a common duct access.

With reference now to FIG. 7, another embodiment of device 110 is illustrated. Device 110 is provided monolithically with two separate compartments, now designated by the reference numerals 111 and 112, which are arranged so as to work in parallel, each compartment being associated with a respective plunger 116a and 116b. A common access 140 to needle 122 protrudes from the bottom wall 121 of compartments 111 and 112. A metering section can be utilized with each plunger 116a, 116b, in similar fashion to that of FIGS. 4 to 6.

It is evident that in other embodiments not shown in the figures the device can be constituted in practice by two separate parts, a first part composed of the support structure of the device in which it is integrated and a second part, which is separate from the first and is accessible by the practitioner and in which the compartments with respective liquids are present; the compartments can be connected to the needle for example by virtue of one or more flexible tubes (not shown).

As seen in the embodiment of FIGS. 1 to 6, the device of the present invention is composed, like a normal pyrogen-free and sterile syringe, by a chamber inside of which is a movable plunger. The chamber is divided by a movable partition dividing the two compartments, inside of which are present the respective physiological washing solution and the anticoagulant solution. The plunger, upon activation, is capable of infusing the physiological solution contained in the first compartment by transferring the pressure through the second compartment and the partition which separates the two compartments. The partition is provided so that once it has ended its stroke for the infusion of the physiological solution it comes into contact with (piercing) to open a connection through the partition between the compartments so as to allow the anticoagulant solution contained in the second compartment to enter the lumen of the catheter under the thrust of the plunger. Once the infusion of the anticoagulant solution has ended, disconnection of the device results in the lumen of the catheter being closed by the closure plug which is already mechanically coupled onto the catheter proximal end.

The use of the device according to the present invention in order to provide maintenance treatment of a catheter, is carried out by the following steps:
 (a) opening the sterile package containing the syringe and removing it;
 (b) disconnecting the medical device from the proximal end of the catheter, thus exposing the lumen;
 (c) connecting the syringe to the catheter end to establish fluid communication with the distal end of the duct or needle;
 (d) sequentially infusing, in a single step, first the physiological washing solution and then the anticoagulant that is already preloaded in the syringe compartment to the precisely desired volume for the lumen of the catheter that is being closed; and
 (e) disconnecting the syringe, with consequent separation and closure of the catheter lumen by the closure plug previously incorporated into the syringe's distal end.

The total number of operations or steps performed with the device of the present invention according to the method of the present invention, is distinctly less than half of the steps performed with conventional methods.

Accordingly, the procedure with the present inventive device is characterized by a reduced risk of infections contamination of the catheter, reduced handling of the catheter with concomitant reduced risk of contamination of the practitioner in the case of work on a patient affected by an infectious condition, such as hepatitis B and C or HIV-related infections; more practical closure in much shorter times; and, minimal errors linked to inaccuracies in the procedure and in the infused volumes, since the operations performed are sequential and inherent to the device itself.

FIGS. 8 to 20 illustrate a third embodiment of syringe assembly in accordance with the present inventive device. A syringe assembly 210 is similar to the device 10 of FIGS. 1 to 6 in that the syringe 218 has a support structure 215 defining a chamber 219 having two compartments 211, 212 in series, and a plunger 216 at the proximal end for activation by the practitioner to express the liquids therefrom, via a duct 217 and needle 222 at the distal end.

Referring firstly to FIGS. 8 to 13, as in syringe 18, the second compartment 212 has a distal end defined by a second movable partition 220. However, in syringe assembly 210, the first compartment 211 also has its distal end defined by a first movable partition 241. Needle 222, preferably non-coring, is secured in duct 217 (see FIGS. 10 and 17) through distal section 221, is more elongate than needle 22 of syringe 18 and has sharp but non-coring tips at both its distal and proximal ends 242,243. The needle's proximal tip 243 extends proximally into an empty distal section 244 of chamber 219.

Figure 11:
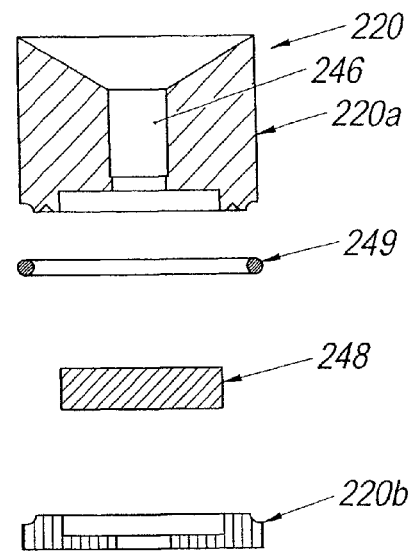
FIGS. 11 to 13 are sectional views of the movable partitions of the syringe of FIGS. 8 to 10, with FIG. 11 being an exploded view of the proximal partition.
Figure 12:
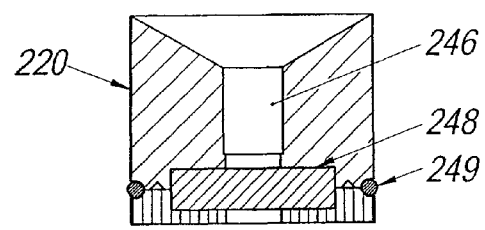
Figure 13:
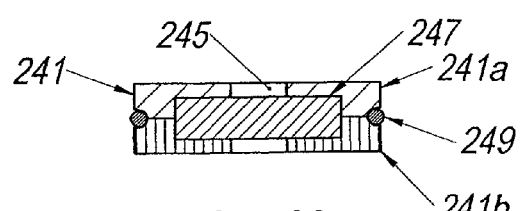
Figure 14:
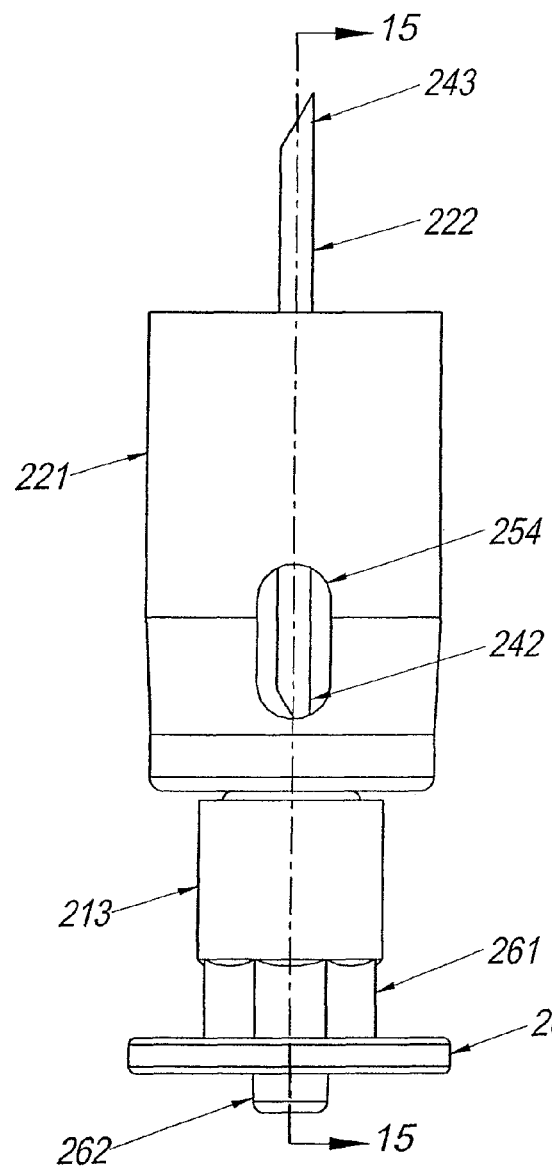
FIGS. 14 and 15 are isometric and longitudinal section views of the distal sub-assembly of the syringe assembly of FIGS. 8 to 13, with FIG. 15 taken along lines 15-15 of FIG. 14.

Best seen in FIGS. 11 to 13, first and second movable partitions 241,220 comprise proximal and distal body portions 241a,241b;220a,220b (through which extend respective passages 245,246) that are affixed to each other such as by bonding or welding to entrap respective transverse pierceable membranes 247,248 that occlude passages 245,246. Membranes 247,248 may be made of resealable material such as, for example, silicone or polyisoprene. O-rings 249 are provided around first movable partition 241, second movable partition 220 and distal end 250 of plunger 216, for establishing respective seals with the interior wall of chamber 219 of the syringe 218. The support structure may be made of, for example, polycarbonate, and the distal section 221, plunger 216 and movable partitions 220,241 may be of, for example, polyvinylchloride.

As the plunger is activated, the liquids in both compartments are pressed distally to move both movable partitions 220,241 distally and toward the needle's proximal tip 242, where the membrane 247 in the first movable partition 241 for first compartment 211 is urged through empty chamber section 244 a certain distance and is pierced by the proximal tip 243 of the needle for the liquid in the first compartment to be expressed from the syringe. Air remaining in empty chamber section 244 after the needle first penetrates the first movable partition membrane 247, is purged via, for example, small dimensioned grooves (not shown) in the sidewall of duct 217 outside of needle 222, and innocuously into plug-receiving chamber 226 to exit the syringe assembly, as plunger 226 is pressed farther distally. Upon evacuation of the liquid in the first compartment 211, the membrane 248 for the second movable partition 220 is pierced by the needle's proximal tip 243 for expression of the liquid in the second compartment 212 from the syringe via duct 217 and needle 222.

Figure 10:
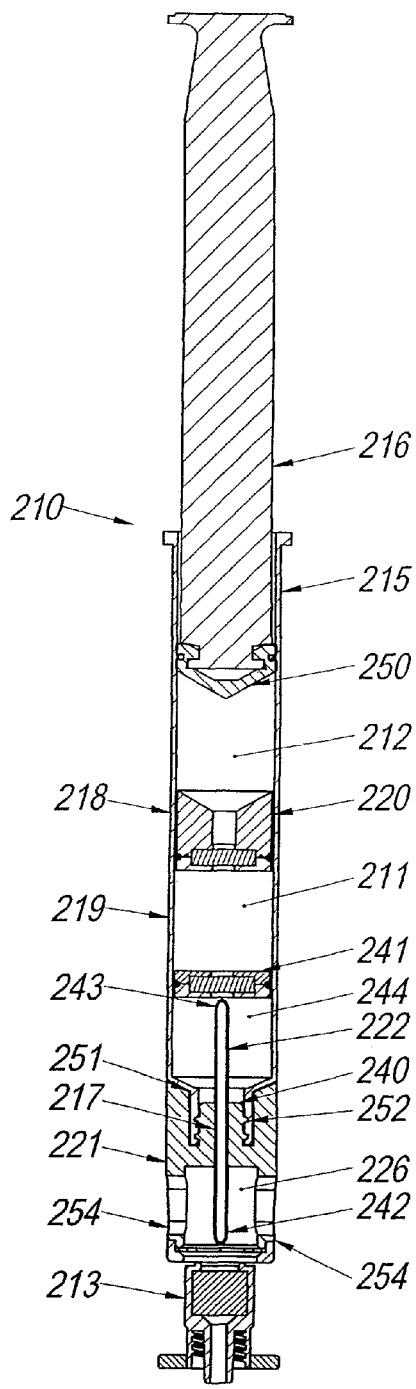
FIG. 10 is a longitudinal section view of the syringe assembly of FIG. 8.

Now, with reference to FIGS. 14 to 20, the distal end of syringe assembly 210 will be described in detail. Distal section 221 is assembled and affixed to support structure 215 distally of empty chamber section 244 (FIGS. 10 and 17); preferably, threads 252 are provided around an axially extending flange 240 of distal section 221 which is received into support structure flange 251 having complementary threads; flange 240 helps to center and properly orient the needle 222 along the longitudinal axis of the syringe assembly. In FIGS. 9 and 10 it is seen that an axially extending small diameter flange 251 extends distally from the distal end of the chamber 219. Duct 217 extends through distal section 221, and needle 222 is affixed to distal section 221 within duct 217 (preferably by force-fit to permit air venting around the needle as aforesaid), projecting distally to distal tip 242 and proximally to proximal tip 243; initially, proximal tip 243 resides in empty chamber section 244, and distal tip 242 resides in plug-receiving cavity 226 of distal section 221 recessed from the distal end thereof. Distal section body 253 preferably includes at least one aperture 254 through a side wall thereof adjacent the distal end of distal section 221 in communication with plug-receiving cavity 226 and enabling the practitioner to visually observe the distal tip 242 of needle 222 for assurance of expression of liquid (see FIG. 14), as is crucial for eliminating the possibility of expression of air into a medical device when the syringe is utilized.

To prevent inadvertent activation of the plunger 216, a removable clip 270 such as is shown in FIG. 8, may be installed at manufacturing when the liquids are loaded into the respective compartments. Clip 270 would snap around the plunger and be positioned between proximal flange 271 of support structure 215 and proximal plunger flange 272, and would be removed by the practitioner when syringe assembly 210 is to be utilized. Also, it is preferred to provide a removable clip 275 that would snap around support structure 215 and around closure plug 213, also installed at manufacturing. Clip 275 would be positioned between proximal flange 271 of support structure 215 and ring 265 of closure plug 213; clip 275 preferably would sufficiently grip support structure 215 to resist axially distal movement therealong. Clip 275 would also serve to secure closure plug 213 to the syringe assembly 210 during shipping and handling, and would be removed by the practitioner after plunger 216 would be moved incrementally distally to assure liquid exits the needle's distal tip 242, whereafter closure plug 213 would be pressed by the practitioner proximally into plug-receiving cavity 226 whereat distal tip 242 of needle 222 would penetrate membrane or plug 231 to extend into the distal end of passage 263 of closure plug 213, as seen in FIG. 18.

Figure 15:
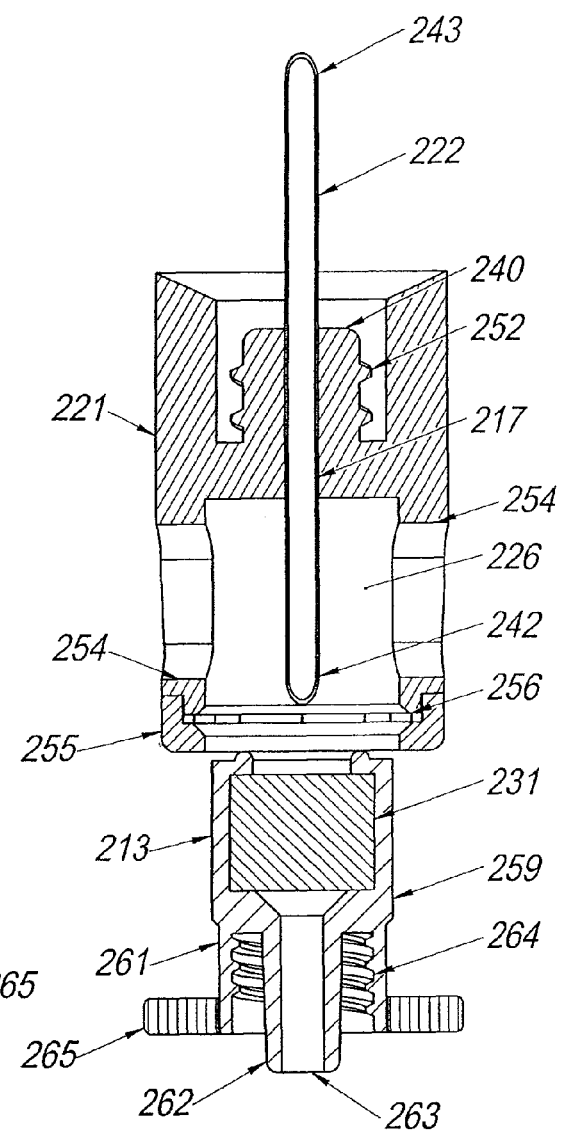
Figures 16, 17:
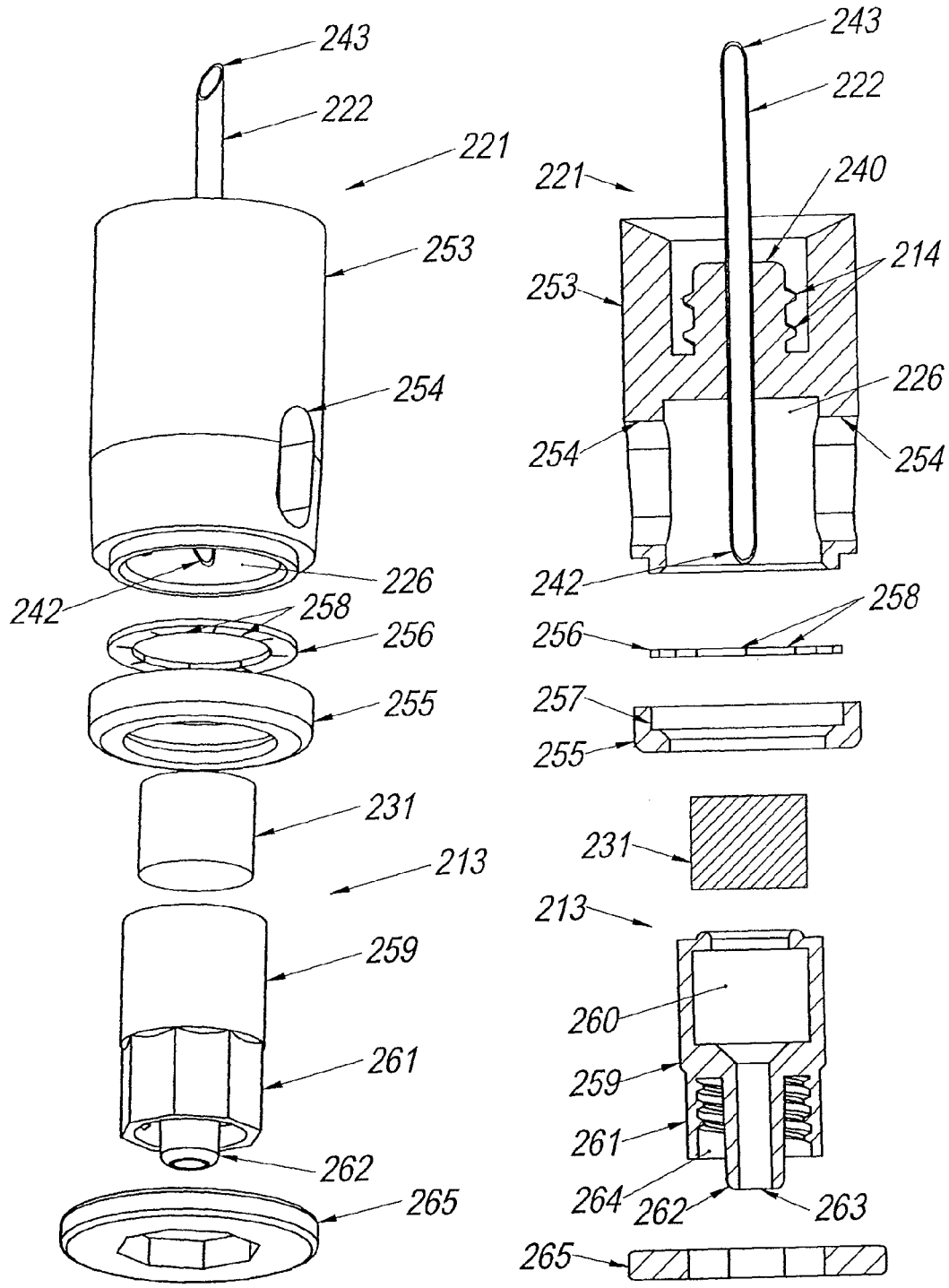
FIGS. 16 and 17 are exploded isometric and cross-sectional views of the distal subassembly of FIGS. 14 and 15.

At the distal end of distal section body 253 of distal section 221 is a cap collar 255 secured thereto such as by bonding or welding, in turn securing in place a plug-gripping ring 256 that is best seen in FIGS. 15 to 17, that is secured against axial movement within a ring seat 257 (FIG. 17) defined between the cap collar and the distal end of the distal section body. Plug-gripping ring 256 preferably includes an array of short radially inwardly extending tabs or fingers 258 that are deflectable, and which are comparable to releasable securement tabs 27 of FIGS. 1 and 2. Fingers 258 can be seated in a corresponding annular groove (not shown) around the outside surface of closure plug 213. Plug-gripping ring 256 can be of a material such as, for example, polytetrafluoroethylene.

Closure plug 213 is movable by the practitioner from an initial or first position, proximally toward the distal section to a second position in which it is disposed within plug-receiving cavity 226, as seen in FIG. 18. Closure plug body 259 is shown to have an interior chamber 260 within which a membrane or plug 231 of resealable material is contained. Plug 231 is pierceable by distal tip 242 of needle 222 when syringe 218 is to be used by a practitioner. An example of a material for plug 231 is silicone, and another is polyisoprene. The outer diameter of plug body 259 is selected to just enter the entrance to distal section 221 through cap collar 255. At the distal end of closure plug 213 is an outer flange 261 and an inner and longer axially extending flange 262 through which a passage 263 extends that will establish fluid communication with another medical device such as catheter 280 whose proximal end 281 is shown in FIGS. 18 and 19 received into threaded receiving recess 264 between outer flange 261 and inner flange 262. Preferably, outer flange 261 has an outside diameter less than the diameter of the proximal portion of the closure plug, so that the gripping fingers 258 are distal of the resulting ledge between the proximal and distal ends of the closure plug facilitating retention within the plug-receiving cavity 226, so that fingers 258 must be deflected against spring bias when closure plug 213 is removed from plug-receiving cavity 226 of the support section. Also, optionally, a grippable ring 265 may be affixed to the distal end of outer flange 261 so that ring 265 can be gripped by the practitioner to withdraw closure plug 213 from the support structure in order to separate the catheter from the syringe.

In FIGS. 18 to 20, operation of the syringe assembly 210 is depicted. In FIG. 18, the closure plug has been pressed fully into the plug-receiving cavity, and proximal needle tip 243 has penetrated membrane 247 of first movable partition 241 for the practitioner to assure that all air has been eliminated from the duct 217; catheter proximal end 281 is shown aligned to be connected to the syringe assembly, a luer fitting 282 having been affixed to the catheter proximal end, as is conventional. The catheter proximal end 281 has been connected to the syringe assembly in FIG. 19 such that the inner flange 262 having been received into the lumen 283 of the catheter as the luer fitting has been received into threaded recess 264 and establishing fluid communication with lumen 263 of the catheter; FIG. 19 also is shown after the plunger 216 is in its fully activated position, needle proximal tip 243 has accessed second compartment 212, and the liquids in the syringe have been completely expressed into the catheter. After completion of the maintenance treatment of catheter 280, as shown in FIG. 20, the syringe assembly 210 is disconnected from the catheter proximal end 281, and closure plug 213 remains affixed to luer fitting 282 and has been released by ring 256 and removed from distal section 221 of the syringe assembly, all so that plug 231 seals the opening at the catheter proximal end 281 thereafter. Closure plug 213 can thus remain affixed to the luer fitting 282 until being removed therefrom for further medical procedures in which the catheter is intended.

In view of the above, in practice it has been found that the inventions thus described achieve the intended aim and objects. The inventions are susceptible of numerous modifications and variations, all of which are within the spirit of the invention and the scope of the appended claims; all the details may furthermore be replaced with other technically equivalent elements, without departing from the broad inventive concept hereof. In practice, the materials used, so long as they are compatible with the specific use, as well as the dimensions, may be any according to the requirements and the state of the art.

What is claimed is:

1. An arrangement for expression of liquid into an opening of a liquid-receiving device by a practitioner, comprising:

a support structure including at least one compartment for containing a liquid therein and further defining a plug-receiving cavity at the distal end thereof, and further including a distal body section which defines the plug-receiving cavity distally of a distal wall, the distal wall traversing the distal end of an empty compartment distally of the at least one liquid-containing compartment, and the arrangement further including a duct extending through the distal body section within which is affixed a needle that extends from the distal end of the at least one liquid-containing compartment through the empty compartment and through the duct into the plug-receiving cavity through which liquid is to be expressed, wherein the distal body section includes at least one aperture through a side wall thereof;

a plunger activatable with respect to the at least one compartment for expression of the liquid from the compartment and into the liquid-receiving device; and a closure plug containing a transverse sealing membrane and having an exposed liquid receiving device connection section, wherein the closure plug is removably attached within the plug-receiving cavity via a non-threaded, releasable securement arrangement within the plug-receiving cavity and independent of the resealable membrane, wherein upon insertion of the closure plug into the plug-receiving cavity, the distal needle tip projects distally of the transverse sealing membrane of the closure plug, and wherein the distal body section of the support structure includes a cap collar affixed thereto at its distal end, the cap collar and distal body section adjacent thereto defining a ring seat wherein a plug-gripping ring is contained that includes an array of gripping sections extending radially inwardly a short distance to be engaged by side surfaces of the closure plug, comprising the securement arrangement, to establish a friction fit therewith when the closure plug is urged into the plug-receiving cavity.

2. The arrangement of claim 1, wherein the support structure is adapted to be manually held and the plunger is adapted to be manually activated.

3. The arrangement of claim 1, wherein the securement arrangement is defined between the distal end of the distal body section and the closure plug.

4. The arrangement of claim 1, wherein the closure plug includes a practitioner-grippable annular ring surrounding its distal end for facilitating removal of the closure plug from the support structure.

5. The arrangement of claim 1, wherein the closure plug includes a larger diameter proximal section having a first diameter and an outer flange extending distally therefrom having a second diameter less than the first diameter, and the gripping sections engage the closure plug outer flange upon urging of the closure plug into the plug-receiving cavity, such that the gripping sections must be deflected against spring bias for the larger diameter proximal section of the closure plug to be removed from the support structure distal end, for enhanced securement of the closure plug within the plug-receiving cavity.

6. The arrangement of claim 5, wherein the outer flange of the closure plug is dimensioned and configured to be coupled to the liquid-receiving device, and the closure plug further includes an inner flange extending distally therefrom surrounding the distal needle tip and sized to enter an opening into the liquid-receiving device.

* * * * *